United States Patent
Larsen

Patent Number: 6,051,018
Date of Patent: Apr. 18, 2000

[54] HYPERTHERMIA APPARATUS

[75] Inventor: Lawrence E. Larsen, Albuquerque, N.Mex.

[73] Assignee: Sandia Corporation, Albuquerque, N.Mex.

[21] Appl. No.: 08/904,220

[22] Filed: Jul. 31, 1997

[51] Int. Cl.[7] ........................................ A61F 7/00
[52] U.S. Cl. ..................... 607/96; 607/101; 607/113; 607/154
[58] Field of Search ..................... 607/101–102, 607/154, 156, 113, 96, 98–100; 606/33

[56] References Cited

U.S. PATENT DOCUMENTS

| | | | |
|---|---|---|---|
| 4,934,365 | 6/1990 | Morgenthaler | 607/101 |
| 4,945,912 | 8/1990 | Langberg | 607/101 |
| 5,097,844 | 3/1992 | Turner | 607/156 |
| 5,234,004 | 8/1993 | Hoscoet et al. | 607/116 |
| 5,300,099 | 4/1994 | Rudie | 607/101 |
| 5,301,687 | 4/1994 | Wong et al. | 607/116 |
| 5,344,435 | 9/1994 | Turner et al. | 607/101 |
| 5,369,251 | 11/1994 | King et al. | 219/695 |
| 5,370,676 | 12/1994 | Sozanski et al. | 607/101 |
| 5,480,417 | 1/1996 | Hascoet et al. | 607/101 |
| 5,509,929 | 4/1996 | Hascoet et al. | 607/101 |
| 5,545,137 | 8/1996 | Rudie et al. | 604/96 X |
| 5,549,639 | 8/1996 | Ross | 607/102 X |
| 5,683,382 | 11/1997 | Lenihan et al. | 607/156 X |

OTHER PUBLICATIONS

O. N. Tereshin and V. I, Korniukhin, Design of Coaxial–Line Low–Q Leaky–Wave antennas by the Method of Successive Approximations, Teoreticheskaia Elektrotekhnika, No. 30, pp. 50–60, 1981. (Russian).

*Primary Examiner*—Max Hindenburg
*Assistant Examiner*—Ryan Carter
*Attorney, Agent, or Firm*—V. Gerald Grafe

[57] ABSTRACT

A hyperthermia apparatus, suitable for transurethral application, has an energy radiating element comprising a leaky-wave antenna. The leaky wave antenna radiation pattern is characterized by a surface wave which propagates along an aperture formed by openings (small in comparison to a wavelength) in the outer conductor of a transmission line. Appropriate design of the leaky wave antenna produces a uniform, broadside pattern of temperature elevation that uniformly heats all or part of the periurethral tissues.

16 Claims, 5 Drawing Sheets

HYPERTHERMIA APPARATUS

This invention was made with Government support under Contract DE-AC0494AL85000 awarded by the U.S. Department of Energy. The Government has certain rights in the invention.

BACKGROUND OF THE INVENTION

This invention relates to the field of energy radiation devices for selective application of electromagnetic energy in lossy dielectric media such as biological tissue, and more particularly, to an energy radiating element suitable for urethral insertion for treatment of prostatomegaly such as benign prostatic hypertrophy, prostatitis, and prostate malignancy.

Electromagnetic probe antennas are clinically used in the treatment of non-operable cancer tumors, wherein the probe or an array of probes is invasively inserted into the tumor. Upon the application of electromagnetic power of the appropriate frequency, the cancer cells can be heated and sustained at elevated temperatures (hyperthermia), causing the cells to lose their ability to divide. Hyperthermia treatment is synergistic with radiation therapy and chemotherapy.

Another important application of electromagnetic probe antennas is in treatment of prostatic disease, malignant or benign. Prostatic disease is relatively common in men over 50 years of age. More than 90% of all men develop benign prostatic hyperplasia (BPH) by the eighth decade of life. It is the most common cause of urinary obstruction in men, and 10–20% of men will require prostatic surgery at some time in their lives to relieve obstructive symptoms. Presently, the treatment of choice for symptomatic BPH is surgery. Surgery carries risks, however, especially for the elderly population most commonly associated with BPH.

An important non-surgical BPH treatment involves the transurethral insertion of a radiating antenna. Electromagnetic energy, usually at microwave frequencies, is transmitted through the antenna to heat the surrounding prostate tissue. The procedure, non-surgical and suitable for outpatient performance with minimal medication, has significant advantages over traditional surgical treatments: lower cost, more rapid recovery, reduced recurrence of symptoms.

The energy radiation pattern of the transurethral antenna is a primary determinant of the effectiveness of the treatment. The energy radiation pattern determines the portion of the tissue affected, and the temperature elevation achieved therein. Numerous antenna configurations have been proposed; unfortunately, none produce a uniform radiation pattern. Consequently, proposed antenna configurations can not provide the uniform tissue heating desired for effective treatment.

Some existing transurethral applicators use monopole antennas. See, e.g., Sozanski et al., U.S. Pat. No. 5,370,676; Hascoet et al., U.S. Pat. No. 5,234,004; Hascoet et al., U.S. Pat. No. 5,480,417; Hascoet et al., U.S. Pat. No. 5,509,929. Deficiencies in monopole antenna designs include leakage currents from the radiating element to the feed, and a generally capacitive load to the generator because the needed quarter wavelength length exceeds the length of the prostatic urethra available. Additionally, as described below, monopole antennas produce non-uniform radiation patterns.

Another proposed design used a monopole antenna, twisted into a helix to reduce its physical length. See Turner et al., U.S. Pat. No. 5,344,435. The resulting helical structure radiates from its end, which is undesirable for tissue hyperthermia application. It can also radiates from its sides (broadside radiation). The broadside radiation pattern is non-uniform, however. Also, the resulting helical structure is too large for applications such as prostatic hyperthermia at centimetric wavelengths required by both Federal Communications Commission requirements and tissue penetration and heating characteristics.

Other existing transurethral applicators use dipole antennas. See, e.g., Rudie et al., U.S. Pat. No. 5,300,099; Rudie et al., U.S. Pat. No. 5,545,137. Each arm of the dipole is typically one fourth of the wavelength. One complex dipole design uses a circumferential cut in an outer conductor to feed a dipole resonator, electrically insulated from the outer conductor. See King et al., U.S. Pat. No. 5,369,251. The design also adds capacitive loading to make the dipole electrically longer than its physical length. See King et al., U.S. Pat. No. 5,369,251. The resulting structure still suffers from the non-uniform radiation field pattern shortcomings inherent in dipole antennas, as described below.

Another proposed design used a loop antenna with a choke to prevent current leakage between the feed and the radiating element. See, e.g., Wong et al., U.S. Pat. No. 5,301,687. The circumference of such a loop antenna is usually about a wavelength for efficient operation, making the structure too large for applications such as prostatic hyperthermia.

The utility derived from the electromagnetic structure is the pattern of tissue irradiation. The radiation patterns from a monopole or a dipole are non-uniform. FIG. 1 shows a typical configuration of a catheter 3 disposed in tissue 1 such as the prostate. The energy radiation patterns and consequent tissue heating patterns of various antenna structures along sections transverse 4 to the catheter axis, coincident 6 to the catheter axis, and parallel 5 to the catheter axis are of interest.

FIG. 2(a,b,c) shows the radiation patterns of a typical monopole antenna. The pattern of a monopole is a toroid with a central null. Accordingly, the radiation pattern transverse to the antenna axis comprises twin humps as shown in FIG. 2a. The central null corresponds to the periurethral regions, resulting in minimal heating of the tissues most important to be heated. The radiation pattern along the antenna axis is minimal, corresponding to the monopole's central null, as shown in FIG. 2b. The radiation pattern parallel to the antenna axis exhibits a region of non-zero radiation, corresponding to the region of the tissue penetrated by the monopole antenna's toroid, as shown in FIG. 2c. Accordingly, a doughnut-shaped region of the tissue, at a distance from and symmetric about a specific point along the antenna axis, can be heated by a monopole antenna.

FIG. 3 shows the radiation patterns of a typical dipole antenna. The pattern of a dipole is a swept figure eight with nulls at the center and both ends. Accordingly, the radiation pattern transverse to the dipole axis comprises twin peaks with surrounding nulls, as shown in FIG. 3a. As with the monopole, the central null corresponds to the periurethral regions, resulting in minimal heating of the tissues most important to be heated (the dipole antenna can be reoriented to relocate the null, but the null still leads to reduced heating in part of the periurethral region). The radiation pattern along the antenna axis is minimal, corresponding to the dipole's central null, as shown in FIG. 3b. The radiation pattern parallel to the antenna axis exhibits a region of non-zero radiation, corresponding to the region of the tissue penetrated by the dipole antenna's swept figure eight, as shown in FIG. 3c. Accordingly, a region of the tissue, at a distance from and at a specific point along the antenna axis, can be heated by a dipole antenna.

The non-uniform radiation pattern of these electromagnetic structures relates directly to non-uniformity of heating in the periurethral tissues. Indeed, the field non-uniformity is accentuated in the thermal pattern because the heat is proportional to the square of the electric field distribution in three-dimensions (i.e. the electric field Hermitian). Nonuniform radiation patterns imply nonuniform field effects upon the tissue. Some areas are over treated, some are under treated. The former causes unnecessary injury to normal tissue to increase unwanted side effects such as incontinence whereas the latter leaves a tissue nidus for new growth. Regrowth leads to recrudescence of symptoms, such as urinary obstruction and the need for re-treatment.

There is a need for hyperthermia apparatus incorporating an energy radiating element, suitable for transurethral application, that provides uniform energy transfer to surrounding tissue.

SUMMARY OF THE INVENTION

The present invention provides a hyperthermia apparatus incorporating an energy radiating element, suitable for transurethral application, that provides uniform energy transfer to surrounding tissue. An outer conductor mounts with the outer surface of a dielectric. The dielectric surrounds an inner conductor, electrically insulating the inner conductor from the outer conductor. The inner and outer conductor can be electrically connected at one end. A source of electrical energy can be connected between the inner and outer conductors at the other end. The outer conductor is disposed on the outer surface of the dielectric in an arrangement, where the arrangement maintains electrical connectivity of the outer conductor but results in the outer conductor covering less than all of the dielectric's outer surface.

The arrangement provides apertures in the outer conductor so that the inner conductor, dielectric, and outer conductor form a leaky-wave antenna. The arrangement can comprise holes through the outer conductor, slots through the outer conductor, a spiral cut into the outer conductor, or other structures forming appropriately sized apertures.

Advantages and novel features will become apparent to those skilled in the art upon examination of the following description or may be learned by practice of the invention. The objects and advantages of the invention may be realized and attained by means of the instrumentalities and combinations particularly pointed out in the appended claims.

DESCRIPTION OF THE FIGURES

The accompanying drawings, which are incorporated into and form part of the specification, illustrate embodiments of the invention and, together with the description, serve to explain the principles of the invention.

DETAILED DESCRIPTION OF THE INVENTION

The present invention provides a hyperthermia apparatus incorporating an energy radiating element, suitable for transurethral application, that provides uniform energy transfer to surrounding tissue.

Figure 1:
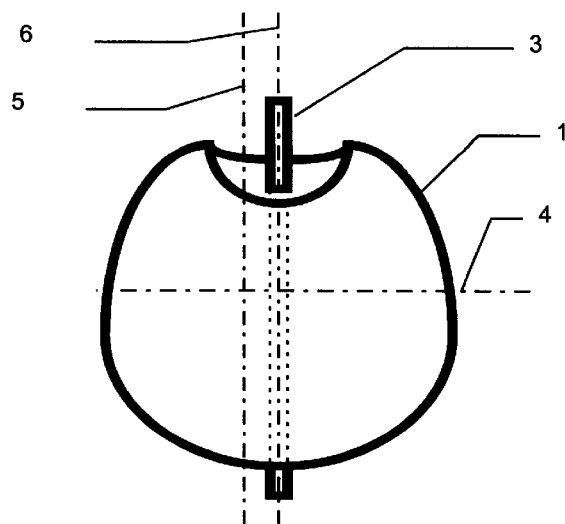
FIG. 1 shows a typical catheter disposed in tissue such as the prostate.
Figure 2A:
FIG. 2($a,b,c$) shows radiation patterns of a typical monopole antenna.
Figure 2B:
Figure 2C:
Figure 3A:
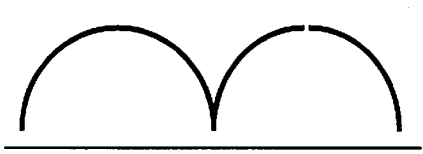
FIG. 3($a,b,c$) shows radiation patterns of a typical dipole antenna.
Figure 3B:
Figure 3C:
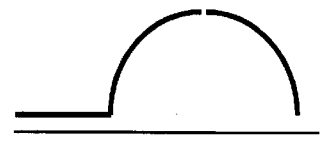
Figure 4:
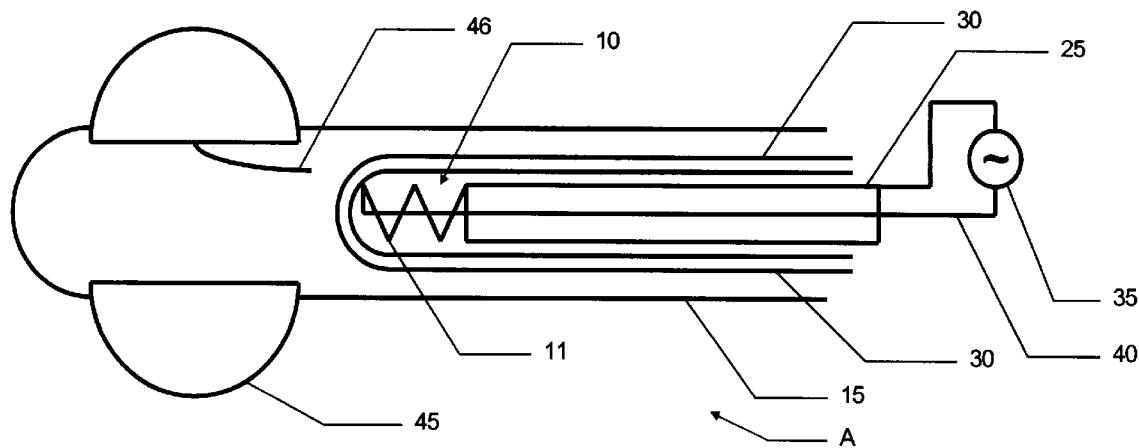
FIG. 4 shows a hyperthermia apparatus comprising a transurethral applicator according to the present invention.

FIG. 4 shows a transurethral applicator according to the present invention. Transurethral applicator A comprises energy radiating element 10 mounted in catheter 15. Catheter 15 insulates energy radiating element 10 and carries cooling loop 30. Applicator A can additionally comprise water balloon 45 to aid in precise positioning. An external transmitter 35 can transmit electromagnetic energy into a transmission line formed by inner conductor 40 and outer conductor 25 of a feed transmission line. A portion 11 of the feed transmission line can be modified to form energy radiating element 10. Cooling loop 30 can comprise temperature monitors and cooling fluid transport mechanism, allowing the tissue temperature to be monitored and excessive heating to be prevented by circulation of cooling fluid through catheter 15.

Figure 5:
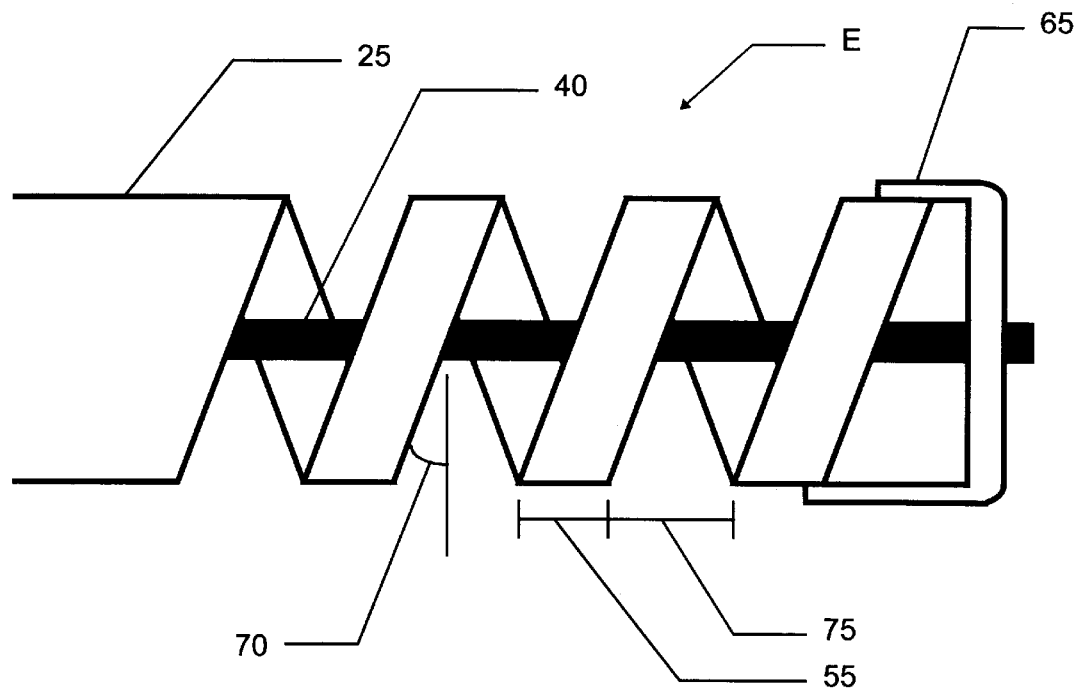
FIG. 5 shows an energy radiating element according to the present invention.

FIG. 5 shows an energy radiating element E according to the present invention. Inner conductor 40 is surrounded by a dielectric material (not shown). Outer conductor 25 surrounds the dielectric material, forming a transmission line with inner conductor 40. Shorting cap 65 connects outer conductor 25 to inner conductor 40. Shorting cap 65 comprises a conductive material (e.g., metal) connected to inner conductor 40 through a hole through the center of shorting cap 65. Shorting cap 65 connects to outer conductor 25 at the edge of shorting cap 65. Shorting cap 65 can completely cover the dielectric (not shown) exposed between the ends of inner conductor 40 and outer conductor 25 to prevent energy radiation from the end of energy radiating element E.

Outer conductor 25 surrounds the dielectric material, and is disposed in a arrangement on the outer surface of the dielectric material, forming part of energy radiating element E. The arrangement maintains electrical connectivity of outer conductor 25, but does not completely shield inner conductor 40. With appropriate outer conductor arrangements, the energy radiating element comprises a leaky wave antenna, characterized by a surface wave which propagates along an aperture formed by openings (small in comparison to a wavelength) in outer conductor 25. The pattern of radiation can be either broadside or endfire. For hyperthermia application broadside radiation is generally desirable. FIG. 5 shows one suitable outer conductor arrangement.

The uniformity of the broadside pattern is a function of the dimensions and orientations of slots 75 and lands 55 in outer conductor 25, the proportioning of open to solid outer conductor 25, and the angle 70 slots 75 make with the axis of inner conductor 40. Optimization of these factors produces a uniform, broadside heat pattern that covers all or part of the periurethral tissues. Some guidance is available for design of leaky wave antennas for free space radiation. See "Design of coaxial-line low-Q leaky-wave antennas by the method of successive approximations," Tereshin and Korniukhin, Teoreticheskaia Elektrotekhnika, no. 30, 1981, pp. 50–60. Radiation in lossy dielectrics such as prostatic tissue, however, is a very different phenomenon. The examples below describe an empirical optimization of the factors. The leaky wave antenna can be covered with a conformal layer of insulation to prevent ingress of fluids between the outer conductor and dielectric as well as to prevent breakdown across slots in the outer conductor, which would otherwise degrade the radiation pattern uniformity.

Figures 6A, 6B, 6C:
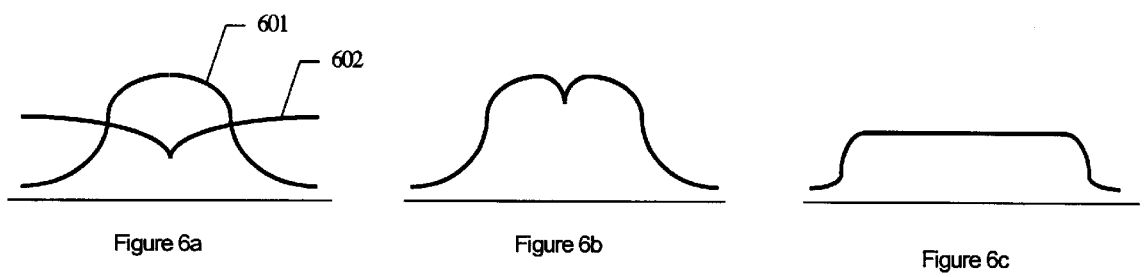
FIG. 6($a,b,c$) shows radiation patterns of an energy radiating element according to the present invention.

FIGS. 6(a,b,c) shows the radiation patterns from an energy radiating element as described above. The radiation intensity 601 transverse to the leaky wave antenna axis, shown in FIG. 6a, decays with increasing distance from the leaky wave antenna axis. The maximum value is near the leaky wave antenna axis, yielding maximum heating in the periurethral region as desired. A cooling loop in the catheter can reduce the temperature 602 of the tissue, with maximum reduction in the region nearest the catheter. Combining the cooling loop effect 602 and the leaky wave antenna effect 601 yields a tissue heating pattern as shown in FIG. 6b. Periurethral tissue is uniformly heated by the leaky wave antenna, while the urethral mucosa is cooled by the cooling loop and thereby protected from heat damage.

Radiation parallel or coaxial with the leaky wave antenna axis is uniform, as shown in FIG. 6c. Tissue heating is consequently uniform along the length of the leaky wave antenna, as desired for effective treatment.

EXAMPLES

Performance evaluation of six energy radiating elements according to the present invention was performed by scanning radiometric measurement of differential heating patterns in a prostate equivalent phantom. The phantom was substantially equivalent to anterior fibromuscular zone of the prostate and had no bladder or non-prostatic urethra associated structures. The energy radiating elements were characterized by diameter, pitch, and land-to-slot ratio. Two diameters were used: about French Gauge 7 and about French Gauge 11. The pitch varied from shallow (roughly 15 degrees) to steep (roughly 60 degrees). The land-to-slot ratio varied from about 1:1 to about 4:1, with slot and land dimensions of, for example, 0.05 inch slots with 0.225 inch lands, 0.125 inch slots with 0.145 inch lands, and 0.1 inch slots with 0.16 inch lands.

The energy radiating elements used Teflon as a dielectric material, and copper as the inner and outer conductors. Those skilled in the art will appreciate other suitable dielectric materials, and other suitable conductor materials, such as silver and gold. A portion of the outer conductor was removed, forming part of a leaky wave antenna. The portion of the outer conductor was removed using conventional photolithography techniques, applied to commercially available RG141 and RG085 semi-rigid coaxial cable. A thimble-shaped shorting cap connected the inner conductor to the outer conductor. The inner conductor extended through a hole in the center of the shorting cap, and was soldered to the cap. The outer portion of the cap was soldered to the outer conductor. The shorting cap prevents radiation from the end of the element. After mounting the shorting cap, the energy radiating element was dipped in a solution of plastic (acrylic), dissolved in toluene. The resulting conformal insulating coating helped prevent fluid contamination of the leaky wave antenna, important to prevent electrolyte from disturbing the leaky wave antenna radiation pattern.

Figure 7:
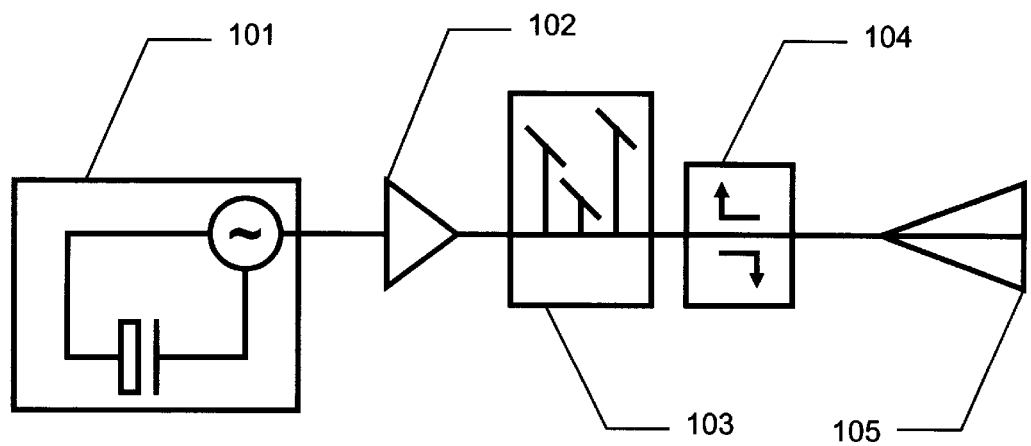
FIG. 7 shows a hyperthermia system according to the present invention.

FIG. 7 shows a system suitable for driving energy radiating elements according to the present invention. A cavity stabilized oscillator (or crystal oscillator) 101 can provide a radio frequency input to a radio frequency power amplifier 102. A tuner 103 can match impedances between power amplifier 102 and energy radiating element 105. Flexible coaxial cable can connect the radio frequency power amplifier to energy radiating element 105. Reflectometer 104 can provide forward and reverse power meters, allowing tuner 103 to be adjusted to minimize reverse power.

The radio frequency performance of each of the six energy radiating elements was tested by infrared scanning radiometry of the phantom along a plane that bisected the pseudo-urethra. Scans were made before and after radio frequency exposure to estimate the heating pattern produced by 30 seconds of irradiation to continuous wave fields at 915 MHz and 10 W. The difference image is a map of the electric field Hermitian. The best energy radiating element, using a leaky wave antenna, produced more uniform heating than previous applicators using monopole or dipole antennas. The most uniform heating was produced by the smaller diameter (French Gauge 7), the greatest pitch (60 degrees), and the smallest land-to-slot ratio (1:1). Within each diameter group, uniformity of heating degraded with reduced pitch and increased land-to-slot ratio. The land-to-slot ratio of 1:1 used with French Gauge 7 diameter yielded slots about 50% larger than the diameter of the outer conductor. The resulting structure has flexibility desirable for prostatic application.

Figure 8:
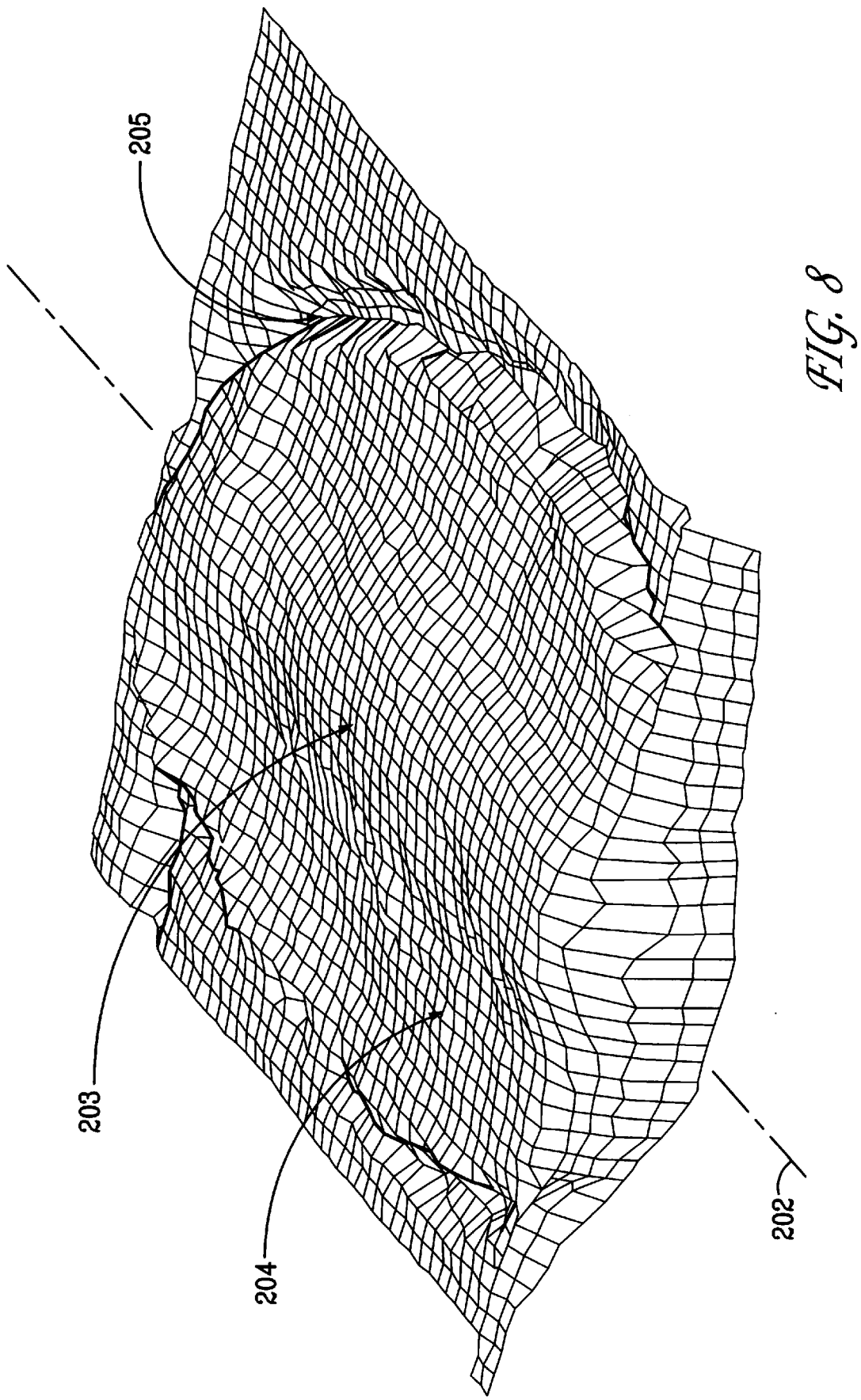
FIG. 8 shows the measured heating pattern for one energy radiating element according to the present invention.

FIG. 8 shows the measured heating pattern for one energy radiating element. A leaky wave antenna was disposed substantially along leaky wave antenna axis 201. The heating pattern 203 along leaky wave antenna axis 201 is uniform along leaky wave antenna axis 201, and decays uniformly 204 with increasing distance from leaky wave antenna axis 201. Discontinuities 205 correspond to physical boundaries of the phantom.

Figure 9:
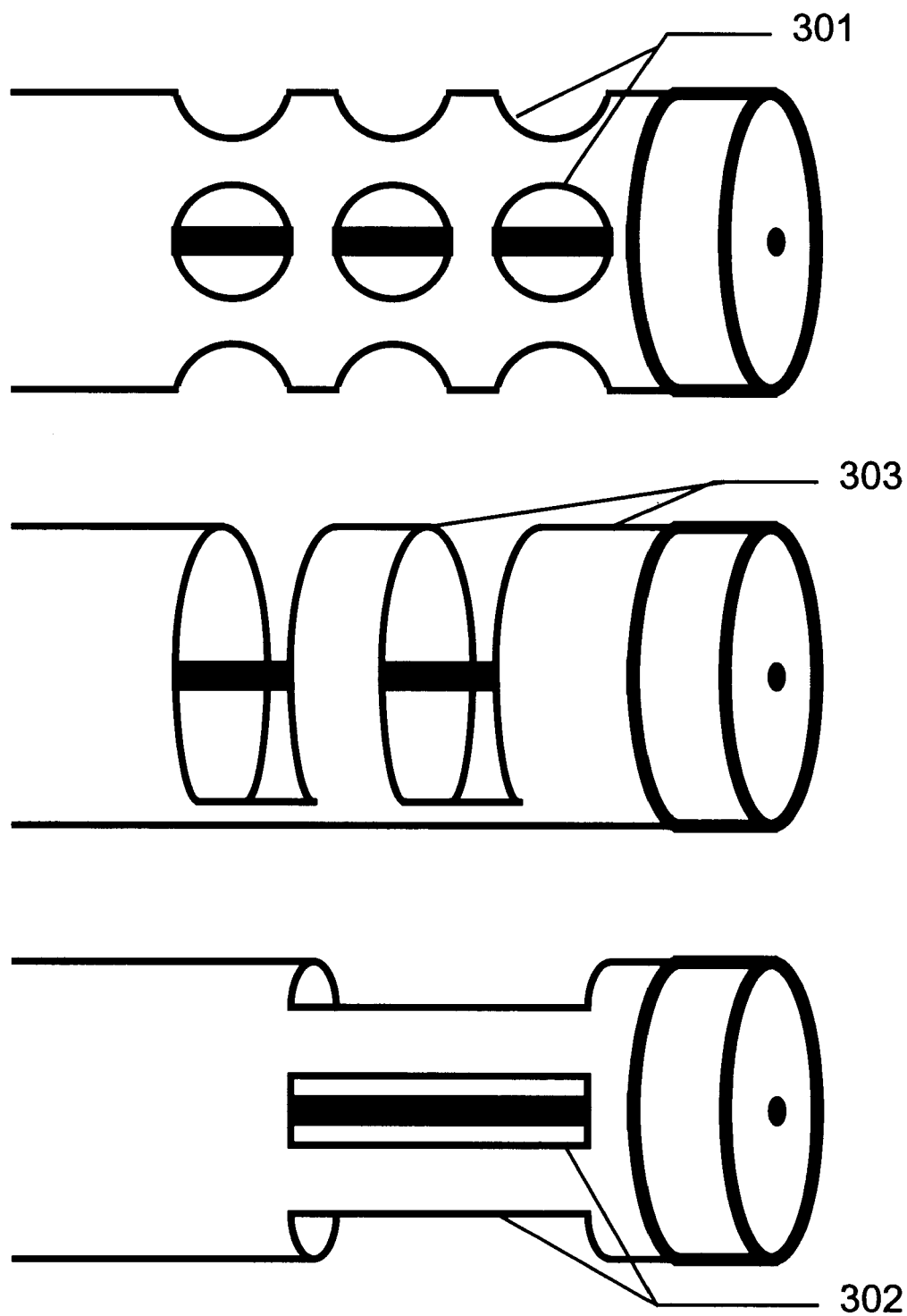
FIG. 9 shows energy radiating elements according to the present invention.

FIG. 9 shows several other example leaky wave antenna configurations. Holes 301, slots 302, and segmented rings 303 can provide apertures in an outer conductor to form an energy radiating element comprising a leaky wave antenna. The radiation pattern of the leaky wave antenna can depend on the dimensions and properties of the conductors, the dielectric, and the imposed electromagnetic wave.

The particular sizes and equipment discussed above are cited merely to illustrate particular embodiments of the invention. It is contemplated that the use of the invention may involve components having different sizes and characteristics. It is intended that the scope of the invention be defined by the claims appended hereto.

We claim:

1. A hyperthermia apparatus comprising a catheter and an energy radiating element comprising a TEM-mode leaky wave antenna.

2. The hyperthermia apparatus of claim 1, further comprising a cooling loop mounted with the catheter.

3. The hyperthermia apparatus of claim 2, further comprising a temperature sensor mounted with the catheter.

4. A hyperthermia apparatus, having an energy radiating element comprising a TEM-mode leaky wave antenna, wherein the leaky wave antenna comprises an inner conductor, an outer conductor, a dielectric disposed between the inner conductor and the outer conductor, wherein a portion of the outer conductor has a spiral shape, and wherein the combination of the dielectric and the outer conductor and the inner conductor define a transmission line having a characteristic impedance and terminated in an impedance discontinuity.

5. A hyperthermia apparatus, having an energy radiating element comprising a TEM-mode leaky wave antenna, wherein the leaky wave antenna comprises a length of coaxial cable, and a) wherein a spiral-shaped portion, extending a distance from a first end of the coaxial cable, of the outer conductor is removed, and b) wherein the outer conductor is electrically connected to the inner conductor near the first end of the coaxial cable.

6. A hyperthermia apparatus comprising:

a) a dielectric disposed along an axis and having an outer surface defining a cross-section perpendicular to the axis;

b) an outer conductor, having first and second ends, mounted with the dielectric outer surface, dispersed in an arrangement maintaining electrical conductivity between the first and second ends and covering less than all of the dielectric outer surface; and c) an inner conductor, having first and second ends, mounted with the dielectric so that the dielectric prevents electrical contact between the inner and outer conductor except at the ends, where the first end of the inner conductor is electrically connected to the first end of the outer conductor, and where the second end of the outer conductor and the second end of the inner conductor are adapted for connection with an electromagnetic energy source.

7. The hyperthermia apparatus of claim 1 wherein the arrangement is chosen from the group consisting of:

a) a spiral extending a predetermined distance from the first end of the outer conductor;

b) a plurality of rings of conductive material, separated from each other by at least a first distance, and electrically connected to each other by additional conductive material;

c) a sheath of conductive material pierced by a plurality of spaced apart holes therethrough; and d) a sheath of conductive material interrupted by an opening therethrough.

8. The hyperthermia apparatus of claim 1 wherein the dielectric comprises Teflon.

9. The hyperthermia apparatus of claim 1 wherein the first end of the inner conductor is connected to the first end of the outer conductor by a shorting cap comprising a metal surface connected to the first end of the inner conductor and to the first end of the outer conductor, where said metal surface completely covers dielectric exposed between first end of the inner conductor and the first end of the outer conductor.

10. The hyperthermia apparatus of claim 1, further comprising a covering defining a volume containing the dielectric, the outer conductor, and the inner conductor, preventing fluid communication into the volume.

11. The hyperthermia apparatus of claim 10, wherein the first end of the inner conductor is connected to the first end of the outer conductor by a shorting cap comprising a metal surface connected to the first end of the inner conductor and to the first end of the outer conductor, where said metal surface completely covers dielectric exposed between first end of the inner conductor and the first end of the outer conductor.

12. A hyperthermia apparatus comprising:

a) a radio frequency generator;

b) a catheter;

c) a dielectric, mounted with the catheter, disposed along an axis and having an outer surface defining a cross-section perpendicular to the axis;

d) an outer conductor, mounted with the catheter, having first and second ends, mounted with the dielectric outer surface, dispersed in an arrangement maintaining electrical conductivity between the first and second ends and covering less than all of the dielectric outer surface; and e) an inner conductor, mounted with the catheter, having first and second ends, mounted with the dielectric so that the dielectric prevents electrical contact between the outer and inner conductor except at the ends, where the combination of the dielectric and the outer conductor and the inner conductor define a transmission line having a characteristic impedance, and wherein the first end of the inner conductor and the first end of the outer conductor provide an impedance discontinuity at the corresponding end of the transmission line, and where the second end of the outer conductor and the second end of the inner conductor are connected to the radio frequency generator.

13. The hyperthermia apparatus of claim 12 wherein the catheter comprises a covering defining a volume containing the dielectric, the outer conductor, and the inner conductor, preventing fluid communication into the volume.

14. The hyperthermia apparatus of claim 12, wherein the catheter comprises a temperature monitor and a cooling loop.

15. The hyperthermia apparatus of claim 12, wherein the catheter comprises a covering defining a volume containing the dielectric, the outer conductor, and the inner conductor, preventing fluid communication into the volume, and wherein the catheter comprises a temperature monitor and a cooling loop.

16. A hyperthermia apparatus comprising:

a) a dielectric disposed along an axis and having an outer surface defining a cross-section perpendicular to the axis;

b) an outer conductor, having first and second ends, mounted with the dielectric outer surface, dispersed in an arrangement maintaining electrical conductivity between the first and second ends and covering less than all of the dielectric outer surface; and c) an inner conductor, having first and second ends, mounted with the dielectric so that the dielectric prevents electrical contact between the inner and outer conductor except at the ends, where the combination of the dielectric and the outer conductor and the inner conductor define a transmission line having a characteristic impedance, and wherein the first end of the inner conductor and the first end of the outer conductor provide an impedance discontinuity at the corresponding end of the transmission line, and where the second end of the outer conductor and the second end of the inner conductor are adapted for connection with an electromagnetic energy source.

* * * * *